United States Patent [19]

Witzel et al.

[11] Patent Number: 4,865,607
[45] Date of Patent: Sep. 12, 1989

[54] TIBIAL PLATE FOR A KNEE-JOINT ENDOPROSTHESIS

[76] Inventors: Ulrich Witzel, Wittener Strasse 73d, 5600 Wuppertal 2; Christoph von Hasselbach, In der Distelkuhle 3, 4300 Essen 1, both of Fed. Rep. of Germany

[21] Appl. No.: 99,235

[22] Filed: Sep. 18, 1987

[51] Int. Cl.⁴ .............................................. A61F 2/38
[52] U.S. Cl. ...................................... 623/20; 623/18
[58] Field of Search ................................ 623/16–23; 433/171–175

[56] References Cited

U.S. PATENT DOCUMENTS

| 3,473,222 | 10/1969 | Kester | 433/173 |
| 4,055,862 | 11/1977 | Farling | 423/20 |
| 4,195,368 | 4/1980 | Patrichi | 623/18 |
| 4,479,271 | 10/1984 | Bolesky et al. | 623/20 |
| 4,673,407 | 6/1987 | Martin | 623/20 |

FOREIGN PATENT DOCUMENTS

| 0010527 | 4/1980 | European Pat. Off. | 623/20 |
| 0046926 | 12/1982 | European Pat. Off. | |
| 2304988 | 8/1973 | Fed. Rep. of Germany | |
| 2810748 | 3/1978 | Fed. Rep. of Germany | |
| G8136619.1 | 5/1982 | Fed. Rep. of Germany | |
| 8136619 | 5/1982 | Fed. Rep. of Germany | |
| 2585236 | 1/1982 | France | 623/20 |

OTHER PUBLICATIONS

Dubell Taschenbuch für den Maschinenbau, pp. 378–379 Marks' Mechanical Engineers' Handbook, Sixth Ed., McGraw-Hill Book Company (excerpt)--Chapter 5, pp. 47–50.
Article "Biomechanische Gesichtspunkte zur Konstruktion von Kniegelenkendoprothesen" by W. Thomas, (med-orthop.-Techn. 6/81)

Primary Examiner—Richard J. Apley
Assistant Examiner—David J. Isabella
Attorney, Agent, or Firm—Herbert Dubno; Andrew Wilford

[57] ABSTRACT

A tibial plate for a knee-joint endoprosthesis has a reinforcement member capable of distributing the joint forces uniformly over the spongiosa so that the spongiosa will not atrophy and is subjected to flexture from the tibial plate which is also supported on a cut section of the corticalis surrounding the spongiosa.

19 Claims, 3 Drawing Sheets

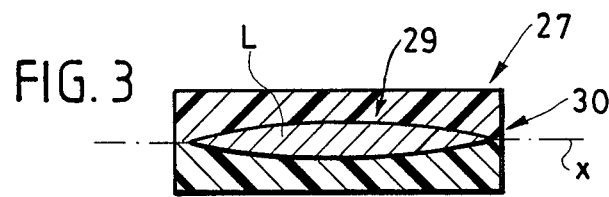
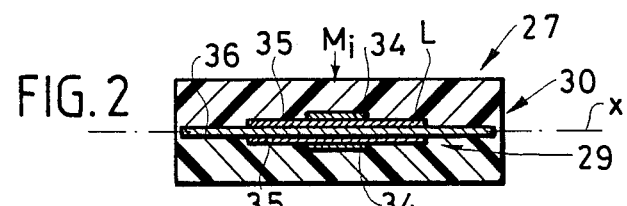
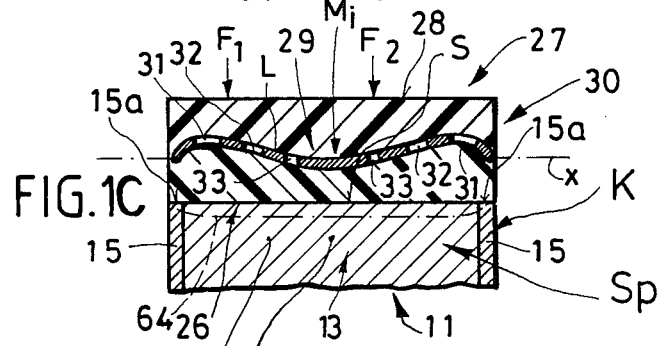
$$\sigma_{Sp} = \sigma_{Sp\,phys} = const.$$
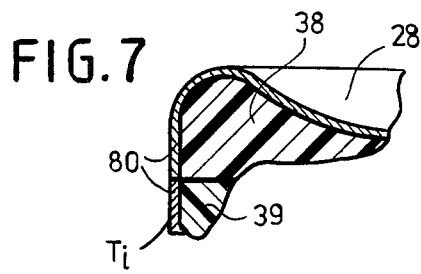

TIBIAL PLATE FOR A KNEE-JOINT ENDOPROSTHESIS

FIELD OF THE INVENTION

Our present invention relates to a tibial plate for a knee-joint endoprosthesis and, more particularly, a tibial plate which is intended to be affixed to the condyle of the tibia and to form a uniform surface upon which a femoral part of the knee joint can slide or roll and which is reinforced to increase the bending resistance of a plastic part forming the sliding or rolling surface. In this description, reference will frequently be made to the sliding action of the femur or a femoral part of a knee-joint endoprosthesis and it will be understood that a reference to the sliding action is intended also to describe a rolling action of the femur or the femoral part of a prosthesis upon the tibial plate.

BACKGROUND OF THE INVENTION

A knee-joint endoprosthesis can have a plate which is affixed to the tibia and which will hereinafter be referred to as a tibial plate and defines one or two sliding surfaces of a uniform character for engagement with the natural end of the femur or with a femoral part of the prosthesis which is affixed to the femur. When two such surfaces are provided, they respectively may constitute the lateral and medial surfaces.

In the case in which the knee-ligament apparatus of the patient remains intact or is comparatively healthy but the knee joint is damaged, a so-called sleigh-type prosthesis may be indicated. In this case, the femoral surfaces forming the knee joint are provided with skids along the condylar rolling or sliding regions, e.g. of steel, while a sliding surface is formed by a tibial plate which is affixed to the tibial.

The tibial plate may be used alone or in conjunction with a total prosthesis. The invention may also be used for knee-joint endoprostheses in which the ligaments have been damaged.

The natural tibial sliding surface is generally formed from solid bone material, namely, the corticalis, which is covered by a cartilage layer. For implantation of a tibial part, this rigid corticalis together with the usually damaged cartilage layer must be removed and the implant fixed on the tibial cross-sectional surface which is then formed. The tibial cross-sectional surface, of course, comprises a central region of spongiosa which constitutes the major part of the area of the bone and is surrounded by an edge region formed by the corticalis.

In the past, the tibial plate has been supported mainly, if not exclusively, on this corticalis shell.

The tibial plates hitherto used generally comprised a synthetic resin layer which formed the sliding surface and had the configuration at its upper side of the normal configuration of the upper end of the tibial plate before removal thereof to accommodate the implant. The underside of this synthetic resin layer was provided with a reinforcement which generally was a completely bending-resistant metal plate on the underside of which small fastening ribs were provided. These ribs could be received in grooves recessed in the spongiosa.

The implanted tibial plate is braced exclusively on the cross-sectional area contributed by the corticalis.

During a rolling and sliding action of the knee joint below the femoral skid or runner and the sliding surface of the tibial plate, all of the joint forces had to be taken up by the corticalis along the edge of the tibial plate.

The spongiosa surrounded by the supported edge region in this system takes up practically no force. As a result, the spongiosa tended to atrophy and recede so that below the metal back of the tibial plate, a cavity tended to form which was progressively filled by connective tissue which was comparatively soft. As a consequence, an attachment of the tibial plate in the region of the spongiosa tended to loosen to the detriment of the junction with the tibia as a whole. In the case of a weak corticalis or a corticalis which, as a result of the cavity formation, weakened with time, there was always the danger of breakage of the corticalis by overloading the knee joint and hence the need for reoperation.

OBJECTS OF THE INVENTION

It is, therefore, the principal object of the present invention to provide a tibial plate for a knee-joint endoprosthesis which will obviate these drawbacks.

Another object of this invention is to provide a tibial plate with improved physiological force distribution to the tibia which will reduce the tendency of the spongiosa to atrophy and recede, and which, in general, will increase the reliability and useful life of a tibial plate.

SUMMARY OF THE INVENTION

These objects and others which will become more readily apparent are attained, in accordance with the invention, in a tibial plate for a knee-joint endoprosthesis which is affixed to a tibia and is slidingly (rollingly) engageable by a femoral part of the prosthesis or the femur itself, the tibial plate comprising at least one plate member, preferably of synthetic resin material, defining a sliding surface for the femoral part of the knee-joint prosthesis and a reinforcement in the plate for increasing the bending resistance of the plate member in response to loading by joint forces. According to the invention, the edge region of the plate is in contact with a section of the corticalis of the tibia but the plate bears upon the spongiosa of the tibia surrounded by the corticalis, the reinforcement having a grider-like stress distribution in the kind of a beam of uniform strength i.e. uniformly distributing to the spongiosa over the area upon which the plate bears a uniform stress resulting from the joint forces and maintaining the deformation of the spongiosa over this area so that it is substantially uniform with displacement of these forces over the surface.

Accordingly, the reinforcement imparts to the synthetic resin plate a degree of elastic bending deformability which causes the spongiosa to be deformed as a result of the bending deformation of the part inwardly of the region supported on the corticalis. As a consequence, the spongiosa in the region thereof in contact with the plate is alternately compressed and relaxed and thus cannot be atrophied.

The reinforcement, however, prevents overloading of the spongiosa to the point that an excessive deformation thereof is possible and could contribute to a loosening of the spongiosa/plate attachment.

An important feature of the invention is that the joint forces result in a uniform stress of the spongiosa and a substantially uniform deformation of the spongiosa across the cross section thereof in contact with the plate. This is achieved, in accordance with the invention, by increasing the bending resistance of the reinforcement inward from the edge regions of the plate supported on the corticalis. The bending of the plate and hence the deformation of the spongiosa can be proportioned to the variation of the modulus of elasticity of the spongiosa over the area thereof in contact with the plate. Even with maximum joint forces, therefore, the maximum permissible spongiosa stress will not be exceeded.

By ensuring a uniform physiological transfer of force to both the corticalis and spongiosa, the entire bone cross section remains intact. Loosening of the attachment of the implant to the tibia is avoided.

While the reinforcement can be formed from an assembly of discrete elements such as granules, fibers, filaments and wires and, in any event, is preferably composed of metal, we prefer to provide the reinforcement in the form of a generally flat reinforcement plate which can be plano-convex or biconvex in cross section. In another alternative, the reinforcement plate can be a stack of plate elements of different lengths the stack having its greatest thickness in a region spaced most distally from the edge region braced around the corticalis.

One way of dimensioning the bending resistance of the plate so that it is greatest in the center and reduced toward the edges supported on the corticalis, is by way of the biconvex cross section described. Alternatively, the reinforcement plate may be bent so that the bends provide greater stiffness in certain regions than in others. In addition, or alternatively, the plate may be of constant thickness and additionally may be provided with perforations whose cross section and distribution establishes a bending resistance which increases with increasing distance from the corticalis-supported edge region.

Preferably, the reinforcement plate is embodied between upper and lower synthetic resin plate members which can be injection molded around the reinforcement plate or, according to the best-mode embodiment of the invention, formfittingly engaged with the reinforcement plate.

In the latter case, means can be provided to form a strip coupling of the upper plate member with the reinforcement plate and of the reinforcement plate with the lower plate member.

A particularly effective approach toward fixing the tibial plate in the tibia is to provide an anchor sleeve of synthetic resin in the spongiosa, the anchor sleeve having a passage opening only at its upper end and a female thread below the upper opening. The passage below the female thread can be a cylindrical guide bore. A screw has a head provided with a circular shoulder bearing upon the reinforcement plate and a male thread below the shoulder engaging the female thread and a cylindrical shaft below the male thread received and guided in the bore. The female thread can be formed by an internally threaded metal ring inset in the sleeve. Surface increasing formations on the sleeve ensure its effective engagement in the spongiosa. These formations may be annular ribs or selftapping threads.

All of the exposed surfaces of synthetic resin of the tibial plate including the sliding surfaces are coated with a ceramic or metal coating, e.g. titanium.

A surface of the lower plate members in contact with the spongiosa can be provided with undercut grooves of dovetail cross section receiving bone tissue. Where additional support means is provided for affixing the tibial plate in the spongiosa, the reinforcement plate can have a reduced bonding resistance in the region of the support means.

BRIEF DESCRIPTION OF THE DRAWING

The above objects, features and advantages of our invention will become more readily apparent from the following description, reference being made to the accompanying drawing in which:

FIG. 1C is a schematic illustration, also in cross section in a sagittal plane, through a tibial plate according to a first embodiment of the invention;

FIG. 2 is a section similar to FIG. 1C but illustrating another embodiment of the tibial plate;

FIG. 3 is a view similar to FIG. 2 illustrating a third embodiment of the tibial plate;

FIG. 7 is a detail section illustrating an aspect of the invention.

SPECIFIC DESCRIPTION

Figure 1A:
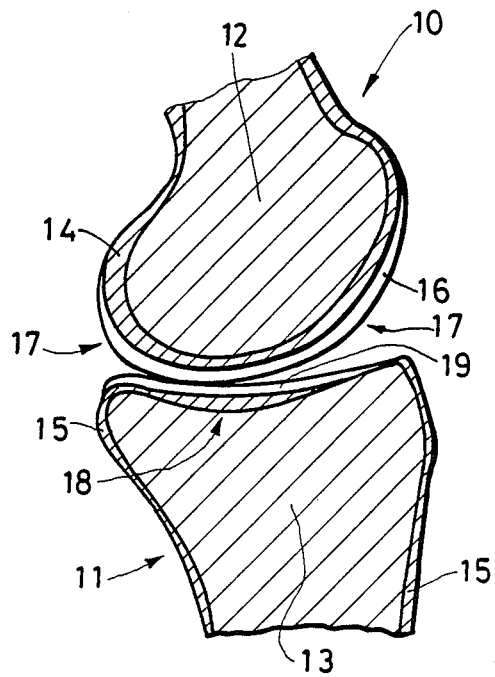
FIG. 1A is a cross sectional view through a knee joint in the sagittal plane and illustrating the knee joint without the ligament apparatus in highly schematic form.
Figure 1B:
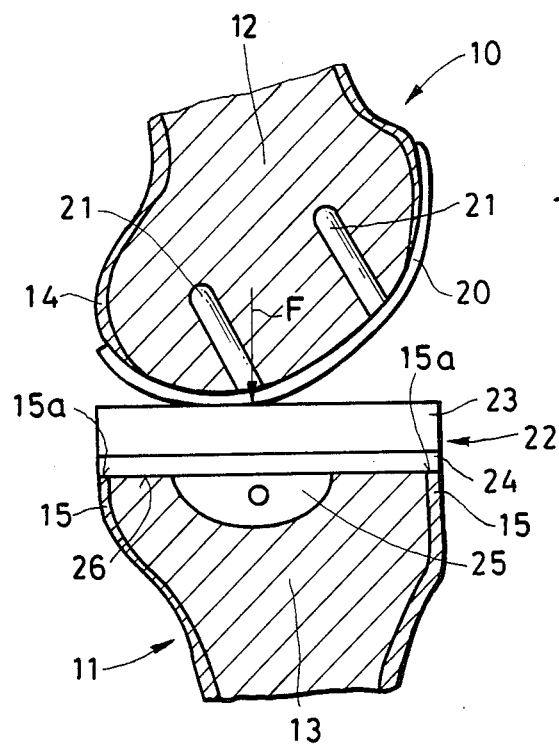
FIG. 1B is a view similar to FIG. 1A showing the prior art sleigh prosthesis which can replace that knee joint.

In FIGS. 1A and 1B, the femur is represented at 10 and in FIGS. 1A and 1B as well as in other FIGURES in which it is shown, the tibia has been illustrated at 11.

Both the femur 10 and tibia 11 have centrally relatively soft bone substance, namely, the spongiosa 12, 13 which is surrounded by very hard bone substance forming an edge region or sheath and represented by the corticalis 14 or 15.

The region of the femur 10 which forms the convex part of the knee joint (FIG. 1A) can have the joint cartilage 16 which extends over the condyle 17. Each femur 10 has two condyles 17 and each condyle 17 engages in a rolling action or movement on the tibial platform 18 which has a sliding layer also in the form of joint cartilage 19.

In a healthy knee joint, the cartilage layers 16 and 17 can engage one another and the joint is supported by relatively hard corticalis. The entire knee joint of FIG. 1A, like that of FIG. 1B is held together by the knee-joint ligaments or the knee-ligament apparatus which has not been shown.

Should there be damage to the knee joint, a sleigh prosthesis can be used and implanted (FIG. 1B). It is possible to provide the prosthesis either as a unicondylar prosthesis for half of the knee joint or a bicondylar prosthesis for the entire knee joint.

In FIG. 1B, the cartilage layer 16 is removed together with a portion of the condylar corticalis of the femur 10 and is replaced by a metal skid or runner 20 which is held in the femur by fastening projections and can be cemented in place.

The cartilage layer 19 and the underlying corticalis of tibia is likewise removed and the cortical surface which lies perpendicular to the axis of the bone then has a corticalis sheathe 15 surrounding the spongiosa 13 onto which the tibial plate of the invention can be placed. The tibial plate 22 shown in FIG. IB is, however, a prior art tibial plate.

This tibial plate comprises a synthetic resin or plastic plate member 23 of polyethylene which is fastened to a relatively thick metal plate 24 provided on its bottom with a projection 25 in the form of a rib which can penetrate into the spongiosa 13.

Since the tibial plate 22 is completely resistant to bending, i.e. cannot be bent by the knee joint forces, the spongiosa 13 below the knee joint takes up no load and thus tends to atrophy. Around the rib 25 and between the spongiosa and lower surface 26 thereof, a space is developed which tends to fill with relatively soft connective tissue. When, moreover, the corticalis shell providing the only support for the joint forces F is overloaded, breakage may occur and the patient may be subjected to loosening of the implant, to considerable pain and to the need for a new operative procedure to correct the problem.

The region in which the corticalis supports the tibial plate has been represented at 15a in FIG. 1B and in other FIGURES.

Consequently, the invention provides, as has been illustrated in FIG. 1C, a tibial plate which comprises a plate member 27 which has a surface 28 adapted to form the sliding surface of the joint and to engage the metal skid or runner on the femur side of the prosthesis. The plastic plate member 27 which may be molded onto and around the membrane metal reinforcing plate 29, which can be a steel sheet, thus is reinforced by the reinforcement plate 29.

While the latter provides an increased resistance to bending or bending stiffness to the plastic plate member 27, it does not completely resist bending.

Indeed, the reinforcement 29 is so formed that it generates the same reaction tension $\sigma_{Sp}$ in the spongiosa wherever the joint force F may be applied. In FIG. 1C the joint force is shown to transit across the sliding surface 28 as represented by the arrows $F_1$ and $F_2$. The girder-like reinforcement thus ensures that the tension applied to the lower surface 26 of the tibial plate 30 will be constant, namely, $\sigma_{Sp} = \sigma_{Sp\ phys} = $ constant. This means that the deformation of the tibial plate in the spongiosa in the kind of a beam of uniform strength will be constant for the application of the knee-joint forces regardless of the location of such application and will also ensure that the physiologically tolerable value of the stress applied to the spongiosa will not be exceeded.

As a consequence, not only is the tibial plate 30 supported on the limited area 15a of the critical cross section, but it is supported over the entire area of the spongiosa 13 surrounded by the corticalis and the spongiosa is thus responsive to the flexing action of the tibial plate over its entire area so that atrophy will not occur and any attachments in and to the spongiosa will be maintained for prolonged periods.

The longitudinal section L of the reinforcement 29 in all of the embodiments is such that the reinforcement acts like a girder to distribute the bending stress uniformly over the entire cross section of the spongiosa regardless of the location of force application from the femur. The reinforcement plate can thus have the cross section of a fishbelly girder i.e. beam of uniform strength or a corresponding bending resistance.

In FIG. 1C, for example, the reinforcement plate is shown to be of uniform thickness over its entire area to be bent to establish a particular bending resistance and to have the bending resistance of the reinforcement plate of FIG. 3 by reason of selective weakening of the reinforcement plate utilizing perforations, 30, 31 and 32 whose perforation widths, cross sections and distribution result in a decrease in perforation area toward the center $M_i$ from the corticalis supporting region 15a. It is possible to provide the reinforcement 29, therefore, so that it has adjacent the corticalis supporting region 15a a substantially lower bending resistance or stiffness then at the center. In general, therefore, the reinforcements 29 of the tibial plates 30 have the characteristic of girders of uniform strength with the consequence that the pressure stress applied to the spongiosa 13 is uniform over the entire area thereof.

The same advantages apply to the combinations of FIGS. 2 and 3 in which the tibial plates are illustrated in an isolated fashion, i.e. without the stylized showing of the tibia 11 of FIG. 1C. The reinforcement 29 of FIG. 2 consists of rigidly interconnected or slidably adjoining stacked reinforcing plate elements 34, 35, 36 of different extents, constituted of metal and around which or onto which the upper and lower synthetic resin plates may be molded. The reinforcing plates 34–36 are so arranged, in a central region $M_i$, most distal from the support region 15a of the corticalis, that the stack has the greatest thickness.

The reinforcement 29 of FIG. 3 functions similarly and the reinforcement is here a biconvex or lenticular-shaped body which can be made from carbon or graphite fibers with or without impregnation with a synthetic resin such as an epoxy resin.

The tibial plates 30 of FIGS. 2 and 3, by reason of the described configurations of the reinforcements, generate uniform stress over the area of the spongiosa.

Each of the reinforcements of FIGS. 1C, 2 and 3 has a longitudinal median plane represented at x and is subjected to joint forces in the direction of the arrows $F_1$, $F_2$ in FIGS. 1C and F in FIG. 1B.

The cross-sectional area of the spongiosa is deformed as represented at S with a uniform pressure stress, the deformation being represented at 64 in FIG. 1C by a dot-dash line.

In all cases, the bending resistance of the reinforcement is controlled by the shape of the reinforcement or the perforation distribution and number so that the bending stress is proportional to the modulus of elasticity across the spongiosa surface engaged by the tibial plate.

Figure 4:
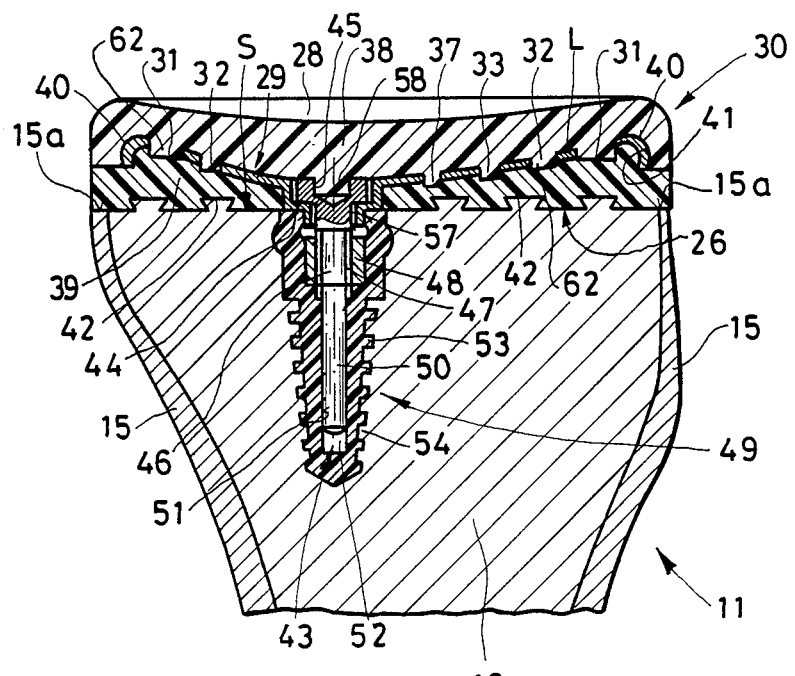
FIG. 4 is a sagittal section similar to FIG. 1B but illustrating only the tibial portion of the prosthesis, i.e. omitting a showing of the femoral part thereof.

In a preferred or best-mode embodiment as illustrated in FIG. 4, the perforations 31–33 of the membrane-like reinforcement 29 are uniformly spaced over the area of the reinforcement but have different widths and hence different cross-sectional area.

The upper synthetic resin element 28 which also forms the sliding surface 28 for engagement with the femoral part of the prosthesis and the lower synthetic resin layer 39 which rests against the spongiosa 13 and is formed with a surface 26 in direct contact with the spongiosa are here constituted as two separately fabricated synthetic resin bodies. The upper body 38 engages over the downwardly and inwardly bent edge 40 of the reinforcement and has an undercut surface 41 which engages the latter in a snap-fitting connection.

The underside 26 of the lower body 39 onto which the reinforcement 29 is snap-fitted has a surface-increasing structure in the form of a multiplicity of dovetail undercut grooves 42 which can interfit with the cut surface S of the spongiosa in a cement-free bond formed by penetration of the spongiosa into the undercut grooves 42. A biological bond is thus the result.

For fastening the tibial plate in place, we can provide a fastening screw 43 which has a male threaded portion 46 immediately below the screwhead with its usual annular abutment surface 44. The screwhead with the abutment surface or shoulder can rest upon an inwardly extending shoulder of the reinforcement plate 29 which is traversed by the screw 43.

A hexagonal socket head 45 can be provided in the head 43 which has, over the length below the threaded portion 46, a cylindrical smooth-surfaced shaft 50. The male thread 46 is spaced below the shoulder 44 as illustrated.

The threaded portion 46 of the screw 43 is received in a female thread 47 formed in a metal threaded sleeve 48 received in a synthetic resin anchor sleeve 49 which can be downwardly tapered.

The smooth-surfaced shaft 50 is slidably received in a cylindrical smooth-walled bore 51 of the sleeve 49 which is closed at its lower end. Below the lower end of the shaft 50, the bore 51 defines an axial free space 52. The sleeve 49 is open only upward at its end turned toward the shoulder 44.

Figure 5:
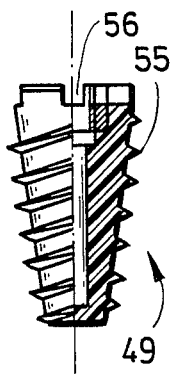
FIG. 5 is an elevational view, partly in section of a plastic sleeve for us in securing the tibial plate in place.

The implant of FIG. 4 is emplaced as follows:

First, the synthetic resin anchor sleeve 49 is seated in the spongiosa 13, e.g. by cementing it in place. To increase the area of contact with the spongiosa, the outer periphery of the sleeve can be formed with annular ribs 53 alternating with grooves 54. Alternatively, the surface-increasing formations may be constituted by a self-tapping thread 55 (FIG. 5) in which case the sleeve is threaded into the spongiosa utilizing a screwdriver whose blade engages in a slot 56, at the upper end of the sleeve 49.

After the sleeve 49 has been implanted, the lower synthetic resin body 39 which can previously have had the reinforcement 29 snapped in place over it, can be seated on the spongiosa. A centering bushing 57 is provided in the reinforcement for this purpose and snugly fits in the upper end of the anchor sleeve 49.

The screw 43 is then inserted and tightened into the anchor sleeve 49 utilizing a hexagonal key engageable in the socket 45 of the screw. The projections 58 of the upper plastic body 38 and corresponding projections 37 can engage in the hexagonal socket and in the perforations 31-33, respectively, as the upper plastic member is snapped over the reinforcement.

The transfer of force is effected in a manner similar to that described in German Patent 33 34 058. The device also serves to take up sheer forces.

The attachment elements 43, 49 also offer advantages with respect to mounting the tibial plate in the sense that can readily provide the bore for the sleeve 49 through narrow gaps in the intact ligament apparatus in a flexed position of the knee. The synthetic resin sleeve 29 and the relatively flat parts of the tibial plate can also be inserted through the narrow gap in the ligament apparatus and assembled within the latter to form the tibial plate portion of the prosthesis.

Figure 6:
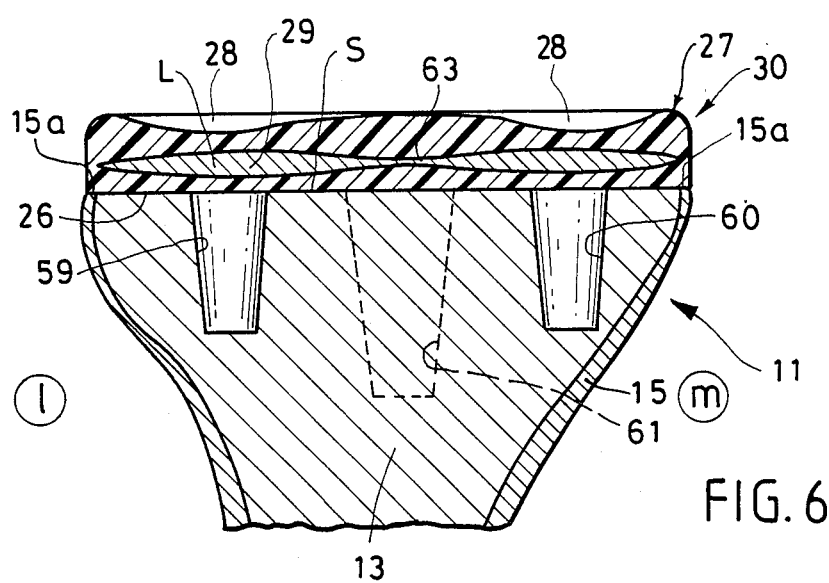
FIG. 6 is a frontal section of a tibial plate showing two slide surfaces thereof which utilizes the principle of the embodiment of FIG. 3 and can be employed alone or as part of a total endoprosthesis.

FIG. 6 shows an embodiment of the invention having two tibial sliding surfaces 28. In that case, a double reinforcement 29 is provided, each part of which has the configuration of the reinforcement of FIG. 3 with a thin connecting zone 63 between these parts of the reinforcement. Each tibial plate element, 64, has in planar view the contour of a somewhat flattened semicircular surface. In this case, two fastening locations 59 and 60 can be provided within the spongiosa, each of which can utilize a screw and anchor as has been described in connection with FIGS. 4 and 5. A single fastening element can also be provided centrally as has been illustrated in broken lines at 61. In FIG. 6, the medial side is represented at m and the lateral side at 1.

FIG. 7 shows all exposed synthetic resin surfaces including the sliding surface 28 of the parts 38, 39, for example, can be provided with a ceramic or metallic coating, e.g. a titanium coating as has been indicated at 80.

We claim:

1. A tibial plate for a knee-joint endoprosthesis affixed to an upper resected end of a tibia having a rim of hard corticalis surrounding a spongiosa mass, the endoprosthesis being slidingly engageable by a femoral part of the prosthesis, the tibial plate comprising:
    an upper sliding surface for the femoral part of the knee-joint endoprosthesis and a lower surface lying on the resected end of the tibia; and
    a reinforcement element in the plate between the upper and lower surfaces thereof for increasing bending resistance of the plate in response to loading by joint forces, the lower surface of the plate having an edge region in contact with the rim of corticalis of the tibia and bearing inward of the edge region upon the spongiosa of the resected tibial end, the reinforcement element increasing in thickness and stiffness inward from the edge region with the plate being sufficiently flexible that it can bend upon application of the joint forces and uniformly distribute to the spongiosa over the area thereof upon which the plate bears a uniform stress resulting from the joint forces and maintaining deformation of the spongiosa over the area substantially uniform with displacement of the forces over the upper sliding surface.

2. The tibial plate defined in claim 1 wherein said reinforcement element is formed from an assembly of discrete elements selected from the group which consists of granules, fibers, filaments, and wires.

3. The tibial plate defined in claim 1 wherein said reinforcement element has a plano-convex section.

4. The tibial plate defined in claim 1 wherein said reinforcement element is a stack of plate elements of different length, said stack having a greatest thickness in a region inwardly of said edge region.

5. The tibial plate defined in claim 1 wherein said reinforcement is embedded between the plate member forming an upper plate member and another plate member forming a lower plate member and disposed between said reinforcement and said corticalis and spongiosa, both said plate members being composed of synthetic resin.

6. The tibial plate defined in claim 5, further comprising means forming a snap coupling releasably securing said upper plate member and reinforcement element to said lower plate member.

7. The tibial plate defined in claim 1, further comprising:
    an anchor sleeve of synthetic resin received in said spongiosa, said anchor sleeve having an upper opening, a female thread below said upper opening, and a cylindrical bore below said female thread; and
    a screw having a head provided with a circular shoulder bearing upon said reinforcement element, a male thread below said shoulder threadedly engaging said female thread, and a cylindrical shaft below said male thread received and guided in said bore.

8. The tibial plate defined in claim 7 wherein said female thread is formed by an internally threaded ring in said sleeve.

9. The tibial plate defined in claim 7, further comprising ribs on an outer surface of said sleeve in contact with the spongiosa.

10. The tibial plate defined in claim 9 wherein said are annular ribs alternating with grooves formed on said sleeve.

11. The tibial plate defined in claim 9 wherein said ribs are selftapping screwthreads formed on said sleeve.

12. The tibial plate define in claim 6 wherein all exposed surfaces of synthetic resin of said tibial plate, including said sliding surface, are coated with a ceramic or metallic.

13. The tibial plate defined in claim 12 wherein said coating is titanium.

14. The tibial plate defined in claim 6 wherein a surface of said lower plate member in contact with said spongiosa is provided with undercut grooves receiving bone tissue.

15. The tibial plate defined in claim 14 wherein said undercut grooves have a dovetail cross section.

16. The tibial plate defined in claim 12 wherein said reinforcement plate extends generally parallel to said sliding surface.

17. The tibial plate defined in claim 16 wherein said sliding surface is upwardly concave.

18. The tibial plate defined in claim 1, further wherein all comprising support means for affixing the tibial plate in said spongiosa, said reinforcement plate having means for reducing bending resistance in the region of said support means.

19. The tibial plate defined in claim 1 wherein said reinforcement plate has a biconvex cross section.

* * * * *